(12) United States Patent
Kruemmel (10) Patent No.: US 8,229,541 B2
(45) Date of Patent: Jul. 24, 2012

(54) MEASURING CONTAINER FOR BIOMAGNETIC MEASUREMENTS

(75) Inventor: Torsten Kruemmel, Walchwill (CH)

(73) Assignee: BMDSys Production GmbH, Magdeburg (DE)

( * ) Notice: Subject to any disclaimer, the term of this patent is extended or adjusted under 35 U.S.C. 154(b) by 351 days.

(21) Appl. No.: 12/578,244

(22) Filed: Oct. 13, 2009

(65) Prior Publication Data

US 2010/0094117 A1   Apr. 15, 2010

Related U.S. Application Data

(63) Continuation of application No. PCT/EP2008/001091, filed on Feb. 13, 2008.

(30) Foreign Application Priority Data

Apr. 11, 2007 (DE) .................. 10 2007 017 316

(51) Int. Cl.
    *A61B 5/05* (2006.01)
(52) U.S. Cl. .................. 600/409; 600/407; 600/410
(58) Field of Classification Search .................. 600/407, 600/409, 410; 324/248
    See application file for complete search history.

(56) References Cited

U.S. PATENT DOCUMENTS

| 4,651,099 A | * | 3/1987 | Vinegar et al. ................. 324/320 |
| 5,152,288 A | * | 10/1992 | Hoenig et al. ................. 600/409 |
| 5,545,844 A | * | 8/1996 | Plummer et al. ............. 174/379 |

FOREIGN PATENT DOCUMENTS

| DE | 23 16 933 A1 | 10/1974 |
| EP | 0 225 954 A | 6/1987 |
| EP | 0 381 273 A1 | 8/1990 |
| EP | 0 528 301 A | 2/1993 |
| EP | 0 359 864 B1 | 12/1993 |
| WO | WO-03/073117 A1 | 9/2003 |

* cited by examiner

*Primary Examiner* — Brian Casler
*Assistant Examiner* — Joel Lamprecht
(74) *Attorney, Agent, or Firm* — Muncy, Geissler, Olds & Lowe, PLLC (57) ABSTRACT

A measuring container is provided, which can be used for biomagnetic measurements, in particular for magnetocardiological measurements. The measuring container comprises an outer screen against electromagnetic high frequency fields and an inner screen against low frequency electromagnetic fields. The measuring container is constructed as a two-chamber system with an outer container comprising the outer screen. A measuring chamber with the inner screen is introduced into the outer container. An antechamber which can be walked into from outside is formed between the inner wall of the outer container and the measuring chamber.

29 Claims, 2 Drawing Sheets

MEASURING CONTAINER FOR BIOMAGNETIC MEASUREMENTS

This nonprovisional application is a continuation of International Application No. PCT/EP2008/001091, which was filed on Feb. 13, 2008, and which claims priority to German Patent Application No. 10 2007 017 316.6, which was filed in Germany on Apr. 11, 2007, and which are both herein incorporated by reference.

BACKGROUND OF THE INVENTION

1. Field of the Invention

The invention relates to a measuring container for biomagnetic measurements which can be used, in particular, for magnetocardiological measurements. Furthermore, the invention relates to a biomagnetic measuring system which comprises a measuring container according to the invention. Such measuring containers and biomagnetic measuring systems can be used, in particular, in the field of cardiology, but also in other medical fields, such as neurology, for example. Other applications are, however, also conceivable.

2. Description of the Background Art

In recent years and decades, magnetic measuring systems which have so far essentially been reserved for basic research have been moving into many fields of biological and medical sciences. In particular, neurology and cardiology are profiting from such biomagnetic measuring systems.

The basis of biomagnetic measuring systems is the fact that most cellular activities in the human or animal body are associated with electrical signals, in particular with electric currents. The measurement of these electrical signals themselves, which are caused by the cellular activity, is known, for example, from the field of electrocardiography. However, in addition to the purely electrical signals, the electric currents are also associated with a corresponding magnetic field whose measurement takes advantage of the various known biomagnetic measurement methods.

Whereas the electrical signals and their measurement outside the body are associated with various factors such as for example, the different electrical conductivities of the tissue types between the source and the body surface, magnetic signals penetrate these tissue regions virtually without interference. The measurement of these magnetic fields and their changes therefore enables conclusions relating to the currents flowing inside the tissue, for example electric currents inside the heart muscle. Thus, measurement of these magnetic fields with high temporal and/or spatial resolution over a particular region enables imaging methods which can, for example, reproduce a current situation of the various regions of a human heart. Other known applications lie, for example, in the field of neurology.

The measurement of magnetic fields of biological samples or patients, and/or the measurement of temporal changes in these magnetic fields constitutes a substantial challenge, however, in terms of measurement technology. Thus, for example, the changes in magnetic fields in the human body which are to be measured in magnetocardiography are approximately one million times weaker than the Earth's magnetic field. The detection of these changes therefore requires extremely sensitive magnetic sensors. In most cases, therefore, superconducting quantum interference devices (SQUIDs) are used in the field of biomagnetic measurements. As a rule, such sensors must typically be cooled to 4° K. (−269° C.) in order to reach or maintain the superconducting state, liquid helium normally being used to this end. The SQUIDs are therefore generally arranged individually or in a SQUID array in a so called Dewar vessel, and are appropriately cooled there. Alternatively, laser-pumped magneto-optical sensors are currently being developed which can exhibit approximately comparable sensitivity. In this case, as well, the sensors are generally arranged in an array in a container for the purpose of temperature stabilization.

The measurement of the extremely weak magnetic fields and/or their changes, which lie in the picotesla or subpicotesla range is naturally extremely sensitive to electromagnetic and magnetic disturbances. The magnetic field detectors of whatever type must be read out, a multiplicity of electronic devices being known for this purpose. However, this readout electronics reacts sensitively to parasitic external electromagnetic fields which can cause strong disturbances. Further disturbances result from the strong signal background of external magnetic fields such as, in particular, micropulsations of the earth's magnetic field or other magnetic fields, in particular temporally varying magnetic fields such as are brought about in multifarious ways in industrial society (for example by movement of large ferromagnetic masses such as trains, lorries etc., by way of example).

Various approaches are known from the prior art to the problem of solving disturbing influences. Thus, for example, WO 03/073117 A1 describes one of the many known devices for measuring magnetic fields in the subpicotesla range. The device uses a SQUID which is coupled inductively to an unscreened gradiometer. The device comprises a filter for filtering magnetically or electrically parasitic radio frequency interference. The aim is thus to lower the requirements on the electromagnetic screening of the measuring device and to enable a SQUID to be operated at all in rugged environments.

However, it has emerged in practice that despite an improved input filtering the signals of biomagnetic measurements can continue to be subject to strong influences from external electromagnetic and magnetic fields, since the abovementioned filters only facilitate the operation of the sensors, but generally have no effect on the electromagnetic disturbances in the frequency range of the biomagnetic signals to be measured. Consequently, it is impossible in practice in many cases to avoid provision of appropriate screening against the electromagnetic and/or magnetic fields. Thus, there have long been known from the civil (for example medical) and military fields eddy current screens against electromagnetic alternating fields which can be both of stationary and of movable configuration. As a rule, low frequency influences have been combatted by screens made from soft magnetic materials which have so far been predominantly of stationary installation.

EP 0 359 864 B1, which corresponds to U.S. Pat. No. 5,152,288, describes a device and a method for measuring weak spatially and temporally dependent magnetic fields. The device comprises a bearing device for holding the examination object, and a sensor arrangement with a SQUID array. Also described is a magnetic screening chamber which has a screening factor of at least 10 for magnetic alternating fields with a frequency of 0.5 Hz, a screening factor of at least 100 for magnetic alternating fields with a frequency of 5 Hz, and a screening factor of at least 1000 for magnetic alternating fields with a frequency of 50 Hz and above. Moreover the screening chamber has a screening factor of at least 1000 for high frequency alternating fields (frequencies greater than 10 kHz).

However, the screening chamber described in EP 0 359 864 B1 is extremely complicated in practice. In particular, there is a need for complicated structural measures in order to integrate the screening chamber into a building, since an appropriate pedestal must be provided which is of the order of magnitude of between 10 and 20 t and is produced from iron-free concrete. In practice, therefore, it is virtually ruled out to change the location of the device or to transport it.

A particular disadvantage of the device described in EP 0 359 864 B1 presides in the fact that despite the complicated screening numerous connections exist between the inner region of the screening chamber and the outer region, these being caused, for example, by leading the patient couch holder through the ground screen, and by further numerous posts led through the screening and by electrical bushings. These bushings have the effect, however, that magnetic and electromagnetic fields are coupled into the interior of the screening chamber and can sensitively impair measurement there.

A particular set of problems of the known screening chambers is, furthermore, in the arrangement of the required measurement electronics and/or of the computer systems required for the evaluation, in particular an image evaluation. If the measurement electronics and the computer systems are arranged entirely or partially in the interior of the screening chamber, they then disturb the measurements of electromagnetic fields generated by the electronics and/or computer systems. In addition, it is thereby impossible in practice in this case to operate the computer systems during the actual measurement, since the operating staff should not stay in the screening chamber during measurement, in order not to influence the measurement. If the measurement electronics and the computer system are, on the other hand, arranged outside the screening chamber, there is a need, in turn, for bushings via which electromagnetic and magnetic fields can be coupled into the interior of the screening chamber.

A further set of problems of such known screening chambers is that it is necessary to ensure that the patient is taken care of at all times, particularly in the field of magnetocardiography. In the case of patients with severe heart problems, in particular, it is necessary to ensure continuous monitoring as well as, in an emergency, also the application of immediate medical emergency measures such as, for example, a defibrillation. However, in the interior of a screening chamber—for example such as the screening chamber described in EP 0 359 864 B1, provision of such care is scarcely possible in practice since, for example, the application of a defibrillator would also simultaneously damage the sensor systems and/or the measurement electronics, and would thus occasion substantial costs. In addition, the space required for emergency medical care is lacking in most screening chambers.

SUMMARY OF THE INVENTION

It is therefore an object of the present invention to provide a screen for biomagnetic measurements which can be used, in particular, for magnetocardiological measurements. The screen is intended, on the one hand, to offer efficient screening against high frequency fields and, preferably, also against low frequency magnetic fields which is, for example, intended to relax the requirements placed on the measurement electronics. At the same time, however, the screening is to be easy to handle, preferably transportable and quick to integrate, in order to open up biomagnetic measurements to a wider field of application than has so far been the case.

It is therefore proposed to configure the screen as a measuring container by contrast with the known screens usually integrated in a housing structure. The proposed measuring container can be used for biomagnetic measurements, in particular in the field of magnetocardiology, but also in other fields of application, and solves, at least to a great extent, the above described problems of the screens known from the prior art. Furthermore, a biomagnetic measuring system is proposed which comprises a measuring container according to the invention in one of the refinements described.

Here, a measuring container can be understood as a container which provides on its own, and preferably without additional static aids, a self supporting construction with an interior which is substantially closed and surrounded by a container wall. As set forth in more detail below, the container is preferably of transportable configuration in order to enable an easy change of location.

The proposed measuring container comprises an electromagnetic outer screen (eddy current screen) against the electromagnetic high frequency fields, and an electromagnetic inner screen against low frequency fields (likewise an eddy current screen). Here, high frequency fields are understood below as fields with a frequency of at least 10 kHz, preferably of at least 100 kHz, up to a maximum of a few gigahertz, for example 10 GHz, whereas low frequency fields are understood as fields with a frequency of below 100 Hz. Again, screening can be provided in the range between 100 Hz and 10 kHz.

In an embodiment, the measuring container is configured not as a single-chamber system, but as a two-chamber system. Consequently, the proposed measuring container comprises an outer container with the outer screen. Introduced into the outer container is a measuring chamber whose wall contains the inner screen. An antechamber which can be walked into from outside is formed between the inner wall of the outer container and the measuring chamber.

By contrast with the prior art, the proposed two-chamber system has a multiplicity of advantages, and enables biomagnetic measuring systems to be extended to numerous novel fields of application. In particular, the proposed measuring container can be used to construct a biomagnetic measuring system, there being held in the measuring chamber a magnetic sensor system, in particular a SQUID system. For example, this magnetic sensor system can be the sensor system proposed in EP 0 359 864 B1, or the sensor system described in WO 03/073117 A1. Furthermore, a measurement electronics which is set up to evaluate the SQUID system or to read out the signals generated by the latter can be coupled to the magnetic sensor system. For example, to this end reference may be made, in turn, to the abovementioned publications. However, it is also possible without limitation to use other sensor systems such as, for example, the abovementioned magneto-optical sensor systems.

Furthermore, it is possible to hold an object couch in the measuring chamber, in particular a patient couch on which the patient or another biological object to be examined can be arranged in an appropriate position.

The evaluation computer which can receive measured data recorded by the measurement electronics can be held outside the measuring chamber, in the antechamber. To this end, the evaluation computer and the measurement electronics can exchange biomagnetic measured data, for example via an appropriate data transmission means. In particular, the data transmission means can comprise an optical fibre connection.

The bipartite division of the measuring container thus on the one hand enables the separation of the evaluation computer from the measurement electronics such that the magnetic sensor system is not disturbed by the evaluation computer or only insubstantially. The number of the bushings into the measuring chamber can, however, be kept low, and it is possible to use optical fibre connections without susceptibility to disturbance. At the same time, the evaluation computer or the data transmission means for the evaluation computer is effectively protected by the outer screen against electromagnetic influences which are therefore scarcely capable of influencing the data reception and the data evaluation, and can simultaneously also not couple them into the bushings into the measuring chamber.

On the other hand, despite the efficient screening described, as a two-chamber system the division enables a substantially improved proximity of the operating staff to the patient. It is true that the operating staff, for example a medical technical assistant, generally cannot see inside the measuring chamber during the actual measurement, since this could substantially interfere with the measurement results. However, the operating staff can stay in the walk-in antechamber, for example in order to operate the evaluation computer and to control the measurement, and thus to be able to intervene easily and quickly should a medical emergency occur inside the measuring chamber. By contrast with present day systems, in which the patient is usually separated by complicated lock systems from operating staff located outside the screening, this constitutes a substantial advance and contributes greatly not only to safety but also to the patient's subjective sense of well being.

This idea can be carried further by setting up the object couch, in particular the patient couch, in such a way that the latter can be brought from the antechamber into the measuring chamber and back. For example, to this end the patient couch can be configured to roll or slide. In this case, the antechamber is appropriately dimensioned in order to be able to hold the patient couch completely. This development has the advantage that, for example, the patient can be brought into the antechamber easily and quickly in the case of a medical emergency and be cared for there as appropriate for a medical emergency, for example by defibrillation, without the magnetic sensor systems located in the measuring chamber being damaged.

Thus, in contrast to conventional magnetic screens, the proposed measuring container and the biomagnetic measuring system constitute a substantial improvement both with regard to the magnetic and electromagnetic screening (and therefore with regard to signal quality), and with regard to user friendliness and the risk to the patient. In addition, it is possible to dispense with complicated lock systems and structural building measures for integrating the measuring container, it being possible to further optimize the signal quality by the minimization or optimization and configuration of the bushings into the interior of the measuring chamber, and by a suitable arrangement of components required in the measuring chamber and of components required only in the antechamber.

As described above, the outer screening is intended to be effective against electromagnetic high frequency fields, that is to say fields above 10 kHz. Here, screening is to be understood in general as an attenuation of the field strength by at least a factor of 2, preferably by a factor of at least 5. It is particularly preferred when the outer screen produces an attenuation of at least 10 dB at frequencies between 100 kHz and 800 MHz, preferably of at least 40 dB and, with particular preference of at least 60 dB. The inner screen preferably produces a screening of at least 10 dB at 50 Hz, preferably a screening of at least 40 dB.

Furthermore, the inner screen can comprise a magnetic screen in addition to the screen against low frequency electromagnetic fields. The magnetic screen can, in particular, have a soft magnetic screen with a screening of magnetic fields below 1 Hz. It is particularly preferred in this case when the screening of magnetic fields amounts to a factor of at least 5 at 0.01 Hz, preferably a factor of 7 to 9. It has proved to be particularly advantageous in this case when use is made for the magnetic screen of soft magnetic materials with a permeability of at least 100, preferably of at least 1000 and, with particular preference, of at least 10 000. For example, the magnetic screen can have at least one of the following materials: a soft magnetic iron alloy, in particular a soft magnetic nickel-iron alloy, in particular a soft magnetic nickel-iron alloy with a nickel content of 75% to 80%. The last named alloy is commercially available in practice, inter alia, under the designation of µmetal or else Mumetal, or under the designation of Magnifer.

A further advantageous refinement of the invention relates to the connection between antechamber and the outer region outside the measuring container. This connection is preferably provided by a door which is let into the wall of the outer container and which preferably likewise has a high frequency screen against electromagnetic high frequency fields. In particular, the high frequency shield can have the above-described screening properties.

In order to improve the patient care, the measuring chamber can also be connected to the antechamber not simply only through an opening or flap, but likewise by an appropriate door (measuring chamber door). The measuring chamber is preferably configured as a walk-in measuring chamber such that, for example, it is not only possible to introduce a lying patient into the measuring chamber, but also possible, for example, for appropriate operating staff to prepare, instruct and care for the patient on the spot in the measuring chamber (before the measurement is carried out). Care of the patient in the event of a medical emergency can also be ensured thereby. In a fashion corresponding to the door of the outer container, the measuring chamber door can also have a screen against the electromagnetic low frequency fields, preferably also against the magnetic fields, for example likewise with the screening properties described above with reference to the inner screen.

A further advantageous development of the present invention is in configuring the measuring container in the simplest and most cost effective way possible, and in facilitating implementation in a building. To this end, it is advantageously possible to configure the outer container in such a way that the latter does not have only the screening properties described, but simultaneously also assumes a supporting, stabilizing function. The outer container thus simultaneously implements the described screening functions and a supporting, static function. Consequently, the measuring container in this advantageous refinement differs, for example, from simple screening claddings of screening spaces, and can, for example, be configured at a stand alone system. The proposed two-chamber system then offers, in particular, the advantage of providing two chambers (antechamber and the interior of the measuring chamber) which lie one behind the other and can also be walked into successively and are nested for the purpose of screening, it being preferred to construct the antechamber such that its length makes a substantial contribution to relieving the floor area stressed by the measuring container.

The outer container can preferably have a layered construction with at least one non-metallic layer and at least one metallic layer. For example, the non-metallic layer can have at least one of the following materials: a polymer foam, in particular a polyurethane foam; a polymer material, in particular a polymer plate, in particular a PVC plate; a wood material, in particular a wood chipboard; a mineral fibre material; a glass fibre material; a resin laminate material, in particular a fibre reinforced resin laminate material.

It is particularly advantageous in this case when the layered construction comprises a sandwich construction. Thus, for example, an inner plate, a fill material and an outer plate can be provided. It is preferred in this case for the inner plate and/or the outer plate to be produced from a metallic material, or to comprise such a metallic material. For reasons of cost and weight, as well as for reasons of ease of processing, aluminium is suggested as one layer of the sandwich construction, since aluminium has good electromagnetic screening properties and is, at the same time, easy to process. Aluminium can also advantageously be used for the outer container and/or also at least partially for the measuring chamber without implementing the idea of the sandwich construction. Alternatively, or in addition, however, copper or alloys can also be used. Other metallic materials can also be used.

The fill material of the sandwich construction can, in particular, contribute to the above-described advantageous supporting function of the outer container. Thus, the fill material can have a wood construction, for example. For example, the sandwich construction can be configured in such a way that a wood construction, for example a construction made from roof battens of a softwood, is assembled to form an appropriate frame. Subsequently, this wood construction is advantageously filled up with a further fill material. For example, to this end the wood construction can be filled up with a polyurethane foam of another of the above-described fill materials, or a combination of the fill materials. After application of the inner plate and the outer plate (these terms also being able to be understood in each case as a combination of a number of plates), the sandwich construction described can be formed therefrom.

It is possible in this way to produce a cost-effective measuring container which satisfies the mechanical requirements placed on the stability of a self-supporting construction, and at the same time effects efficient screening without the need for complicated measures in shaping the building for the purpose of holding the measuring container.

In combination with the above-described sandwich construction, however, it has also proved to be advantageous in conjunction with other configurations of the outer container when the inner and/or the outer screen have at least one of the following metals: aluminium, copper, an aluminium alloy, a copper alloy. In particular, the outer screen can have a metallic layer with a thickness of 0.5 mm to 10 mm, in particular from 1 mm to 5 mm. The inner screen preferably has a metallic layer with a thickness of at least 5 mm, preferably of at least 8 mm.

In particular, by contrast with earlier known screening chambers, the measuring chamber can be held non-concentrically in the outer container. The position of the measuring chamber in said outer container has turned out in practice to be unimportant, and so the division into measuring chamber and antechamber can be undertaken in accordance with the remaining requirements, for example the space requirements placed on the antechamber. For example, it is possible in this way to ensure a patient couch is held inside the antechamber.

A further advantageous development of the present invention takes account of the fact that a defective electrical connection of the outer screen and the inner screen of an interior, or in the present case the measuring chamber, can lead to undesired electrical effects. In an advantageous development of the invention, the empty space between the inner wall of the outer container and the measuring chamber is at least partially filled up with a conductive material in such a way that an electrically conductive connection is produced between the inner screen and the outer screen. Seen in electrical terms, the outer screen in the region of the measuring chamber is in this way a component of the inner screen, this also be accompanied by non-negligible advantages with reference to the screening behaviour at low frequencies. For example, the measuring chamber can be connected via the conductive material to the inner wall of the outer container in the region of an underside of the measuring chamber, the top side of the measuring chamber and a rear wall of the measuring chamber. In this case, for example, only the front side, facing the antechamber, of the measuring chamber would not be in contact with the conductive material. Other refinements are also conceivable, however.

It has proved to be particularly advantageous in this case when the conductive material has a deformable conductive material. For example, this can be a plastically and/or elastically deformable conductive material. Also possible are materials which are deformable only in a first state, and subsequently become cured such as, for example, conductive epoxides. It is particularly preferred when the deformable conductive material comprises a conducting paste. Also conceivable is the use of a silver conducting paste or other pastes or liquids filled with conductive particles. In conjunction with the use of aluminium as base material for screening, the pastes or liquids are advantageously to contain chemicals which solve the problem of aluminium oxide.

As set forth above, the proposed measuring container is distinguished, in particular by its simple and cost effective construction. Thus, in particular, the outer container can simultaneously take over the function of electromagnetic screening, and the supporting function. For example, with reference to its mechanical loadability the outer container can comply with current container standards, for example ISO 1496-2 standard. In order to ensure rapid transport and in order, for example, to facilitate integration of the container in existing premises, the measuring container can be configured, in particular, as transportable measuring container and have transport elements (for example appropriate eyes or other transport elements known from container technology), which enable the intervention of a transport device.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
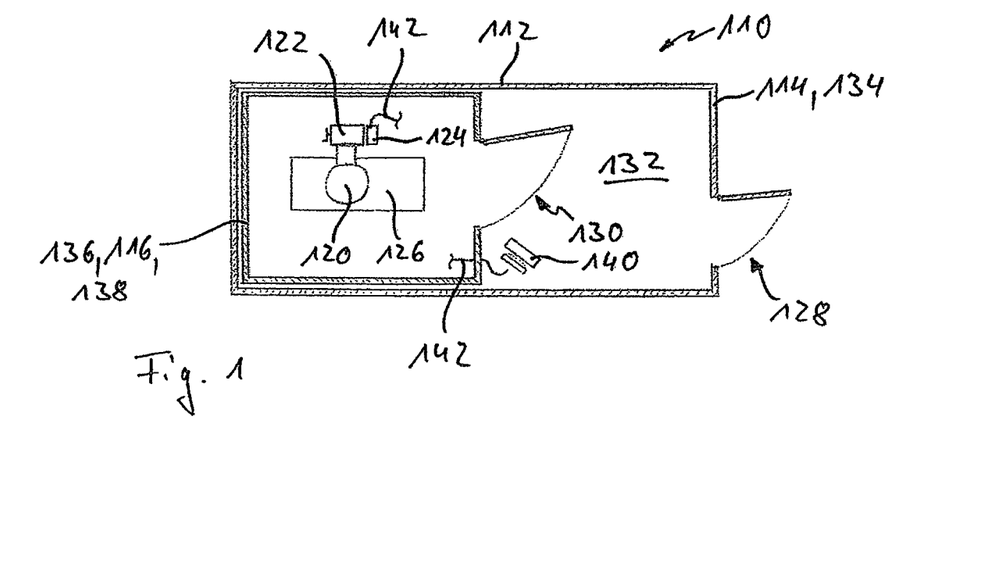
FIG. 1 shows a sectional illustration of an exemplary embodiment of an inventive biomagnetic measuring system with an inventive measuring container in a view from above.
Figure 2:
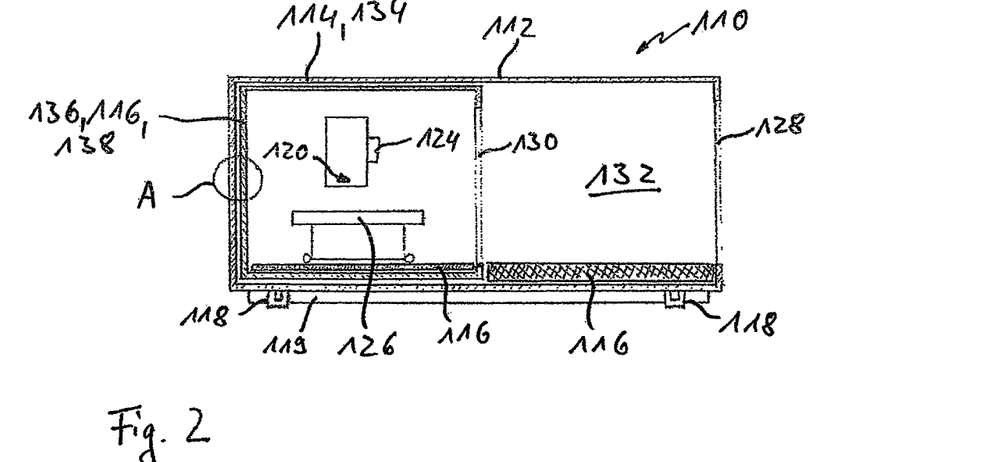
FIG. 2 shows the biomagnetic measuring system in accordance with FIG. 1 in a sectional illustration from the side.

An exemplary embodiment of an inventive biomagnetic measuring system 110 is illustrated in FIGS. 1 and 2. The biomagnetic measuring system 110 comprises an exemplary embodiment of an inventive measuring container 112 which is illustrated in FIG. 1 in a sectional illustration in a view from above, and is illustrated in FIG. 2 in a sectional illustration in a view from the side.

According to the invention, the measuring container 112 can be constructed as a two-chamber system and comprises an outer container 114 into which a measuring chamber 116 is introduced.

The outer container 114 can, for example, be designed as a standard container and can, for example, be loaded onto a lorry, fastened there and transported in this way. To this end, for example, it is possible to provide on the outer container 114 appropriate transport elements 118 which are known to the person skilled in the art. For example, these can be standard transport elements by means of which the measuring container 112 can be raised and/or fixed on a lorry, a goods wagon or a ship. Four such transport elements 118 can be provided, for example. Furthermore, the outer container 114 serves the purpose of distributing the weight in order to distribute the total weight of the measuring container 112 and the apparatus held therein over a corresponding area.

In the present exemplary embodiment, the transport elements 118, which are illustrated only diagrammatically in FIG. 2, are components of a subfloor construction 119 which is arranged below the outer container 114. For example, this subfloor construction can comprise an aluminium frame which is connected to the outer container 114 by fastening measures known to the person skilled in the art. For example fastening can be effected by a few screws e.g. eight to twelve screws. The subfloor construction can, for example, enable a standardized transport on a ship or a lorry, can comprise forklift truck pockets for the engagement of forklift trucks, can, for example, hold pluggable feet in the case of temporary storage, and can contribute to distributing the weight of the measuring container 112.

Finally, if the measuring container 112 is to be integrated in a stationary fashion, for example inside a building on a concrete plinth or another floor structure, the subfloor construction 119 can preferably be removed with a few manipulations, for example by loosening the connecting screws. The measuring container 112 without the subfloor construction 119 can then be connected, in turn, to the building or to a special concrete or foundation plate separate from the building, doing so by screwing and/or by using other fastening means such as bolts, by bonding, welding or by being concreted in.

Various further elements of the biomagnetic measuring system are held in the measuring container 112. Thus, the biomagnetic measuring system 110 comprises, in particular, a magnetic sensor system 120 which is held on an appropriate frame 122 such that it can be displaced and/or positioned vertically. In this exemplary embodiment, the magnetic sensor system 120 is formed by a multiplicity of superconducting magnet sensors (SQUIDs) which are held in a Dewar (merely indicated in the figures). This Dewar is, in turn, suspended on the frame 122 such that its height can be adjusted. The behaviour will be similar were the sensor system 120 to be formed by a multiplicity of magneto-optical sensors in a temperature controlled container.

Coupled in a known way to the magnetic sensor system 120 is a measurement electronics 124, which is likewise merely indicated in FIG. 1. As described above, the magnetic sensor system 120 and the measurement electronics 124 can be configured, for example, as set forth in the prior art, for example as described in WO 03/073117 A1. However, other configurations of the sensor system 120 and the measurement electronics 124 are also conceivable and are known to the person skilled in the art.

Located below the magnetic sensor system 120 inside the measuring chamber 116 is a patient couch 126. This patient couch 126 is preferably produced from nonmagnetic material and is movably supported (as indicated merely symbolically in FIG. 2). A lying patient can be positioned on this patient couch 126 in such a way below the magnetic sensor system 120 that his chest area is detected by the magnetic sensor system 120. Magnetocardiographic images of the patient's heart can be taken in this way. Other types of object couches or similar "sample holders" can be used correspondingly for other types of biomagnetic measuring systems.

The measuring container 112 in the exemplary embodiment illustrated in the figures has two doors: a door 128 of the outer container and a measuring chamber door 130. A user of the biomagnetic measuring system 110, for example a patient and/or member of the operating staff, walks into the measuring container 112 through the door 128 and thereby reaches an antechamber 132. The antechamber 132 is separated from the region outside the measuring container 112 merely by the wall of the outer container 114, which has an outer screen 134. As explained above and further discussed below with the aid of FIG. 3, this outer screen 134 serves as an eddy current screen against electromagnetic high frequency fields.

Proceeding from the antechamber 132, the user then enters the interior of the measuring chamber 116 through the measuring chamber door 130. The measuring chamber wall of the measuring chamber 116 comprises an inner screen 136 which, in addition to the outer screen 134, protects the interior of the measuring chamber 116 against electromagnetic influences in the low frequency range. As described above, this inner screen 136 is an eddy current screen in the low frequency range below 100 Hz.

The interior of the measuring chamber 116 is thus doubly protected against electromagnetic disturbances in different frequency ranges by the screens 134, 136. In addition, as likewise discussed below in more detail with the aid of FIG. 3, the inner screen 136 further comprises a magnetic screen 138 in the form of a soft magnetic screen. Consequently, the interior of the measuring chamber 116 is protected both against high frequency, and against low frequency electromagnetic irradiation, and against extremely slowly variable magnetic influences.

The antechamber 132, which has an elongated shape visible in FIGS. 1 and 2, has the effect that even with doors 128, 130 open it is only irradiation from a comparatively small solid angle which can reach into the interior of the measuring container 112, and so disturbances owing to electromagnetic and magnetic influences are additionally suppressed by the geometry of the measuring container 112. In the ideal case, in which the antechamber 132 would have an infinitely long extent (in a horizontal direction in FIGS. 1 and 2), this solid angle at which disturbances could penetrate through the open doors 128, 130, would even be reduced to a vanishingly small solid angle.

The number of the bushings via which the antechamber 132 is connected to the interior of the measuring chamber 116 can be reduced to an absolutely necessary minimum. In particular, the measurement electronics 124 held in the measuring chamber 116 can be connected by an optical fibre connection 142 (illustrated clearly partially in FIG. 1) to further measurement electronics (not illustrated) held in the antechamber 132, and can exchange measured data. Coupling in electromagnetic and/or magnetic noise signals through bushings in the wall of the measuring chamber 116 and/or the inner screen 138 can thereby be reduced to a minimum. Supplying the measurement electronics 124 with power can be performed, for example, by screened plug connectors, for example by screened plug connectors which additionally include filters and which are likewise not illustrated in the figures.

Figure 3:
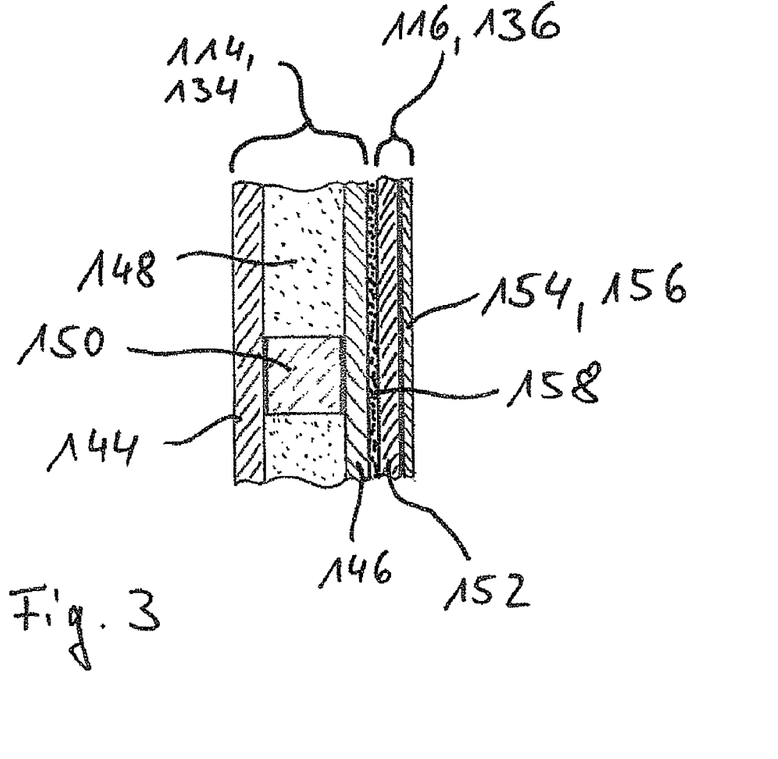
FIG. 3 shows an enlargement of the section of the wall of the measuring container denoted by A in FIG. 2.

As described above, the double screening in the form of the outer screen 134 and the inner screen 136 constitutes a substantial element of the inventive measuring container 112. In order to explain the screens 136, 138 in further detail, the section which is denoted by A in FIG. 2 is shown in FIG. 3 in an enlarged illustration. Here, the section A is selected in such a way that it covers a region in which the wall of the measuring chamber 116, and thus the inner screen 136, are arranged in the immediate vicinity of the wall of the outer container 114, and thus of the outer screen 134.

In the preferred exemplary embodiment illustrated in FIG. 3, the wall of the outer container 114 is produced in a sandwich construction. This sandwich construction is composed of an outer plate 144 made from fibre reinforced resin laminate, and an inner plate 146. For the purpose of providing the outer screen 134 in the form of an eddy current screen against high frequency electromagnetic radiation (frequencies above 10 kHz), the inner plate 146 is produced in this exemplary embodiment from an effectively conducting material. As described above, copper and/or aluminium plates or metal plates with alloys of said elements are particularly suitable to this end. However, it is also possible to use other effectively conducting metallic materials. The thickness of the inner plate 146 is preferably between 1 and 5 mm.

In the sandwich construction illustrated in FIG. 3, the interspace between the two plates 144, 146 is substantially filled up with a dimensionally stable fill material 148, for example once again with a fibre reinforced resin and/or with a polymer foam, for example a polyurethane foam. Furthermore, in this exemplary embodiment there is introduced into the interspace between the plates 144, 146 a wood construction 150 which contributes substantially to the stability of the outer container 114. The wood construction 150 can, however, also be replaced and/or supplemented by an increased stability of the plates 144, 146 and/or of the filling material 148.

It may be pointed out that the region A in FIG. 2 is a wall region of the outer container 114. The construction of the outer container 114 can, however, vary at different regions such that, for example, different constructions are used in the ceiling region of the outer container 114, in the floor region and in the region of the side walls. In particular in the floor region, the outer wall of the outer container 114 can, for example, be of reinforced configuration, and can provide a uniform weight distribution and serve as a weight distribution element.

In this case, the outer container 114 takes over the function of the outer screen 134 against the electromagnetic high frequency fields by means of the inner plate 146 made from effectively conducting material, in particular from aluminium. Furthermore, the construction of the wall of the measuring chamber 116, which takes over the inner screen 136, is illustrated in FIG. 3.

In order to ensure the inner screening 136, the wall of the measuring chamber 116 firstly has a thick plate 152, which is assigned to the wall of the outer container 114. The thickness of this plate 152 is preferably at least 8 mm. This plate 152 therefore contributes substantially to the stability of the measuring chamber 116 and is partially responsible for the stability thereof.

In order to provide the inner screen 136 against low frequency electromagnetic disturbances, it is possible, in turn, to use copper or aluminium as materials. It is also possible, in turn, to use alloys, it being possible, for example, to use copper or aluminium with a small amount of additives, for example with less than 4% of alloyed additives. A plate 152 with the described properties constitutes an effective inner screen 136 with the above-described properties in the low frequency range.

Furthermore, in the preferred exemplary embodiment illustrated in FIG. 3 the wall of the measuring chamber 116 has a magnetic screen 154. Here, the plate 152 serves as supporting structure for installation of this magnetic screen 154. To this end, a plate 156 of a soft magnetic material is applied to the side of the plate 152 facing the interior of the measuring chamber 116. For example, as described above, it is possible to make use to this end of a μ metal plate, for example with a thickness of approximately 1 to 2 mm. However, other soft magnetic materials 156 can also be used.

As a further characteristic, the preferred exemplary embodiment of the screens 134, 136 which is illustrated in FIG. 3 has a large area electrical connection between the two eddy current screens (inner plate 146 and plate 152). To this end, the interspace between the outer container 114 and the measuring chamber 116 is largely filled up in the illustrated region with an electrically conductive fill material 158. This electrically conductive fill material 158 produces an electrical connection between the two screens 134, 136 such that an enhancement of the screening performance comes about in the region of the measuring chamber 116 in the low frequency range, as well.

Conducting pastes are to be named as an example of such electrically conductive fill material 158. Particularly preferred in this case are conducting pastes which are capable of removing or of penetrating insulating surface oxide layers in order to improve the electrical contact between the plates 146 and 152. This is to be remarked, in particular, when use is made of aluminium, which tends to form on the surface an oxide layer which would worsen electrical contact between the plates 146, 152. Particular suitability for the electrically conductive fill material 158 has been shown, for example, by pastes or liquids which contain electrically conductive particles, for example zinc particles, which penetrate this oxide layer (for example by mechanical abrasion and/or by electrochemical decomposition of the oxide layer), and thereby improve the electrical contact. Such electrically conductive fill materials 148 with an antioxidizing effect are marketed, for example, by Ideal Industries GmbH under the designation of "Noalox®". However, it is also possible to use other electrically conductive fill materials with a preferably antioxidizing effect or the effect of removing oxide layers.

The connection between the measuring chamber 116 and the outer container 114 can be made by conventional connections, for example by screwing, by bolts, by welding, by bonding, by plug constructions, or by other configurations known to the person skilled in the art. The construction of the doors 128 and 130 can correspond substantially to the construction of the remaining wall of the outer container 114 or of the measuring chamber 116, but can also be more simply fashioned. For example, the measuring chamber door 130 can be provided merely with an eddy current screen in the form of the plate 152, the soft magnetic screen 156 being dispensed with.

The outer container 114 corresponds to the sandwich construction illustrated in FIG. 3, for example the construction of conventional cooling containers. In this case, a cooling container can, for example, be modified in such a way that the fibre reinforced resin laminate plate normally used as inner plate 146 is replaced by the metallic inner plate 146 which ensures the outer screening 134. A conversion of commercially available containers can be implemented easily and quickly in this way. The subfloor construction of the outer container 114, which preferably has a non-ferromagnetic material can, in particular, be configured in such a way that standard regulations are fulfilled so that the measuring container 112 can be loaded instead of a standard container onto a lorry, for example, can be fastened there and transported, and on the other hand the requirements of a weight distribution element are met.

A working floor 116 made from a plastics material is held on the floor in the interior of the antechamber 132 and of the measuring chamber 116. This working floor 116 can be configured, for example, in such a way that it evens out the difference in level between the antechamber 132 and the interior of the measuring chamber 116. It can thereby be ensured, for example, that the patient couch 126 can be brought from the interior of the measuring chamber 116 into the antechamber 132 without this requiring a threshold to be overcome. The antechamber 132 is therefore preferably dimensioned in such a way that it can hold the patient couch 126 completely. In this way, it is possible in the event of a medical emergency, for example, for the patient couch 126 to be brought into the antechamber 132 quickly, in order to carry out intensive medical measures there such as, for example, a defibrillation which could damage the measurement electronics 124 and/or the magnetic sensor system 120 in the interior of the measuring chamber 116.

The working floor 160 can be fabricated, for example, from a plastics material, for example a PVC laminate. Depending on the application, the working floor 160 can also have additional properties, for example conductive properties, for example in order to prevent electrostatic damage to the measurement electronics 124 by a user. The working floor 160 can, for example, be connected to the wall of the outer container 114 and/or of the measuring chamber 116 by bolts, screws, bonding or similar connecting techniques.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

The invention claimed is:

1. A measuring container for biomagnetic measurements or for magnetocardiological measurements, the measuring container comprising:
    an outer screen configured to shield electromagnetic high frequency fields; and
    an inner screen configured to shield low frequency electromagnetic fields,
    wherein the measuring container is configured as a two-chamber system with an outer container comprising the outer screen, a measuring chamber with the inner screen being introduced into the outer container, and an antechamber that is configured to be walked into from outside and is disposed between an inner wall of the outer container and the measuring chamber, and
    wherein the empty space between the inner wall of the outer container and the measuring chamber is at least partially filled up with a conductive material in such a way that an electrically conductive connection is produced between the inner screen and the outer screen.

2. The measuring container according to claim 1, wherein at frequencies between 100 kHz and 800 MHz the outer screen produces an attenuation of at least 10 dB.

3. The measuring container according to claim 1, wherein the inner screen produces a screening of at least 10 dB at 50 Hz or a screening of at least 40 dB.

4. The measuring container according to claim 1, wherein the inner screen additionally comprises a magnetic screen.

5. The measuring container according to claim 4, wherein the magnetic screen has a soft magnetic screen which effects a screening of magnetic fields at 0.01 Hz by a factor of at least 5.

6. The measuring container according to claim 4, wherein the magnetic screen has a soft magnetic material with a permeability of at least 100.

7. The measuring container according to claim 4, wherein the magnetic screen includes soft magnetic iron alloy.

8. The measuring container according to claim 1, wherein the antechamber can be walked into from outside by a door provided into a wall of the outer container, the door having an eddy current screen configured to shield electromagnetic high frequency fields.

9. The measuring container according to claim 1, wherein the measuring chamber has a measuring chamber door to the antechamber in order to introduce a measurement object into the measuring chamber.

10. The measuring container according to claim 9, wherein the measuring chamber is configured as a walk-in measuring chamber.

11. The measuring container according to claim 9, wherein the measuring chamber door has an eddy current screen configured to shield electromagnetic low frequency fields.

12. The measuring container according to claim 9, wherein the measuring chamber door has a magnetic screen configured to shield low frequency magnetic fields.

13. The measuring container according to claim 1, wherein a wall of the outer container has a layered construction with at least one non-metallic layer and at least one metallic layer.

14. The measuring container according to claim 13, wherein the non-metallic layer has at least one of the following materials: a polyurethane foam; a PVC plate; a wood chipboard; a glass fibre material; or a fibre reinforced resin laminate material.

15. The measuring container according to claim 13, wherein the wall of the outer container has a sandwich construction with an inner plate, a fill material and an outer plate, the inner plate and/or the outer plate having an aluminium plate and/or a copper plate.

16. The measuring container according to claim 15, wherein the fill material comprises wood.

17. The measuring container according to claim 13, wherein the inner screen and/or the outer screen have at least one of the following metals: aluminium; copper; an aluminium alloy; or a copper alloy.

18. The measuring container according to claim 1, wherein the outer screen has a metallic layer with a thickness of 0.5 mm to 10 mm.

19. The measuring container according to claim 1, wherein the inner screen has a metallic layer with a thickness of at least 5 mm.

20. The measuring container according to claim 1, wherein the measuring chamber is held non-concentrically in the outer container.

21. The measuring container according to claim 1, wherein the conductive material comprises an electrically conductive paste or liquid.

22. The measuring container according to claim 1, wherein the conductive material comprises at least one of the following materials: a silver conducting paste; or an anti-oxidizing paste, or a paste filled with conductive metal particles.

23. The measuring container according to claim 1, wherein the measuring container is configured as a transportable measuring container and includes at least one element connectable to a transport device.

24. A biomagnetic measuring system comprising: a measuring container comprising:
- an outer screen configured to shield electromagnetic high frequency fields; and
- an inner screen configured to shield low frequency electromagnetic fields,
- wherein the measuring container is configured as a two-chamber system with an outer container comprising the outer screen, a measuring chamber with the inner screen being introduced into the outer container, and an antechamber that is configured to be walked into from outside and is disposed between an inner wall of the outer container and the measuring chamber;
- the biomagnetic measuring system further comprising a magnetic sensor system in the measuring chamber and at least one electronic measuring system coupled to the magnetic sensor system, and an evaluation computer in the antechamber, the evaluation computer and the electronic measuring system being set up in order to exchange biomagnetic measured data via a data transmission device.

25. The biomagnetic measuring system according to claim 24, wherein the data transmission device comprises an optical fibre connection penetrating the wall of the measuring chamber.

26. The biomagnetic measuring system according to claim 24, further comprising an object couch, the measuring container and the object couch being set up in such a way that it is possible to bring the object couch from the antechamber into the measuring chamber and back.

27. The biomagnetic measuring system according to claim 24, wherein the magnetic sensor system comprises a SQUID system or a magneto-optical system.

28. The measuring container according to claim 7, wherein the soft magnetic iron alloy includes a soft magnetic nickel-iron alloy.

29. The measuring container according to claim 28, wherein the soft magnetic nickel-iron alloy has a nickel content of 75% to 80%.

* * * * *